United States Patent [19]

Lessey

[11] Patent Number: 5,279,941
[45] Date of Patent: Jan. 18, 1994

[54] DETERMINATION OF ENDOMETRIAL RECEPTIVITY TOWARD EMBRYO IMPLANTATION

[75] Inventor: Bruce Lessey, Havertown, Pa.

[73] Assignee: Trustees of the University of Pennsylvania, Philadelphia, Pa.

[21] Appl. No.: 897,706

[22] Filed: Jun. 12, 1992

[51] Int. Cl.$^5$ .................. G01N 33/554; G01N 33/577
[52] U.S. Cl. .................................. 435/7.21; 435/960; 436/510; 436/519; 436/65
[58] Field of Search ............... 435/7.21, 810, 960; 436/510, 519, 548, 65, 814; 530/388.25, 389.3, 391.3

[56] References Cited

U.S. PATENT DOCUMENTS 5,057,604  10/1991  Brown .............................. 530/387

OTHER PUBLICATIONS

Lessey et al "Integrin Adhesion Molecules in the Human Endometrium" J. Clin. Invest. 90:188–195 Jul. 1992.
Lessey et al, abstract #401 from 38th Annual Meeting of the Society for Gynecologic Investigation Mar. 1991.
Lessey et al, abstract from 2nd International Conference on the Extracellular Matrix of the Reproductive Tract May 1992.
Vanderpuye et al "A vitronectin–receptor–related molecule in human placental brush border membranes" Biochem J 280:9–17 Nov. 1991.
Tabibzadeh "Patterns of expression of integrin molecules in human endometrium throughout the menstrual cycle" Human Reproduction 7(6):876 1992.
Getzenberg et al., "The Tissue Matrix: Cell Dynamics and Hormone Action", *Endocrine Rev.*, 11:399–417 (1990).
Albelda et al., "Integrins and Other Cell Adhesion Molecules", *FESEB J.*, 4:2868–2880 (1990).
Buck et al., "Integrin, a Transmembrane Glycoprotein Complex Mediating Cell–Substratum Adhesion", J. Cell Sci. Suppl., 8:231–250 (1987).
Burridge et al., "Focal Adhesions: Transmembrane Junctions Between the Extracellular Matrix and the Cytoskeleton", *Ann. Rev. Cell Biol.* 4: 487–525 (1988).
Hemler, M. E. "VLA Proteins in the Integrin Family: Structures, Functions and Their Role on Leukocytes", *Annu. Rev. Immunol* 8:365–400 (1990).
Rogers and Murphy, "Uterine Receptivity for Implantation: Human Studies", in *Blastocyst Implantation*, Yoshinaga, K. ed., Serono Symposia, pp. 231–238 (1989).
Satyaswaroop et al., "Isolation and Culture of Human Endometrial Glands", *J. Clin. Endocr. Metab.*, 48:639–641 (1979).
Bennett et al., "Inhibition of Fibrinogen Binding to Stimulated Human Platelets by a Monoclonal Antibody" *PNAS*, vol. 80, 2417–2421 (1983).
Kohler and Milstein, "Continuous Cultures of Fused Cells Secreting Antibody of Predefined Specificity" *Nature*, 256: 495–497 (1975).
Noyes et al., "Dating the Endometrial Biopsy", *Fertil. & Steril.*, 1:3–25 (1950).
Lowry et al., "Protein Measurement with Folin Phenol Reagent", *J. Biol. Chem.*, 193:265–275 (1951).

(List continued on next page.)

*Primary Examiner*—Esther L. Kepplinger
*Assistant Examiner*—Nancy J. Parsons
*Attorney, Agent, or Firm*—Woodcock Washburn Kurtz, Mackiewicz & Norris

[57] ABSTRACT

Methods are provided for detecting receptivity of mammalian endometrium to embryo implantation comprising obtaining a sample of the endometrium, contacting the endometrium with a monoclonal antibody for $\beta_3$ integrin and detecting $\beta_3$ integrin in the endometrium. The invention also provides for methods of diagnosing infertility in a mammal and methods of detecting the window of embryo implantation in endometrium. Methods of in vitro fertilization, methods of preventing embryo implantation and a method of monitoring endometrial maturation are also within the scope of the present invention. The present invention is also directed to contraceptives. Diagnostic kits useful in the practice of the methods of the invention are also provided.

32 Claims, 6 Drawing Sheets

OTHER PUBLICATIONS

Laemmli, U. K., "Cleavage of Structural Proteins During Assembly of the Head of Bacteriophage T4", *Nature*, 227:680–685 (1970).

Albelda et al., "EndoCAM:A Novel Endothelial Cell-Cell Adhesion Molecule", *J. Cell Biol.*, 110:1227–1237 (1990).

Hertig, A. T., et al. E.C. "A Description of 34 Human OVA within the First 17 Days of Development"; Am. J. Anat. 98:435–493 (1956).

Navot, D. et al. "Preparation of the Human Endometrium for Implantation", *Ann. N.Y. Acad. Sci.* 622:212–219 (1991).

Navot, D. et al. "An Insight into Early Reproductive Processes Through the in vivo Model of Ovum Donation" *J. Clin. Endocrinol. Metab.* 72:408–414 (1991).

Navot, D. M. "The Window of Embryo Transfer and the Efficiency of Human Conception in vitro", *Fertil. Steril.* 55:114–117 (1991).

Ruoslahti E. et al. "New Perspectives in Cell Adhesion: RGD and Integrins" *Science* 238:491–497 (1987).

Kao, Lee-Chuan et al. "The Human Villous Cytotrophoblast: Interactions with Extracellular Matrix Proteins, Endocrine Function, and Cytoplasmic Differentiation in the Absence of Syncytium Formation" *Developmental Biology* 130, 693–702 (1988).

Martel, D.; "Scanning Electron Microscopy of the Uterine Luminal Epithelium as a Marker of the Implantation Window" in *Blastocyst Implantation*, Yoshinaga, K. ed. Serono Symposia 225–230 (1989).

Schlafke Sandra, et al. "Cellular Basis of Interaction Between Trophoblast and Uterus at Implantation" *Biology of Reproduction* 12, 41–65 (1975).

Tabibzadeh Siamak "Immunoreactivity of Human Endometrium: Correlation with Endometrial Dating" Fertility and Sterility, 54:624–631, No. 4 Oct. (1990).

Yoshinaga Koji; "Receptor Concept in Implantation Research" *Development of Preimplantation Embryos and Their Environment* pp. 379–387 (1989).

Psychoyos A. et al. "Embryo–Endometrial Interactions at Implantation" *Implantation of the Human Embryo* Academic Press Inc. 195–209 (1985).

Anderson T.; "Biomolecular Markers for the Window of Uterine Receptivity" in *Blastocyst Implantation*, Yoshinaga, K. ed., Serono Symposia.

Fay, T. N.; "Human Endometrial Peptides: A Review of Their Potential Role in Implantation and Placentation" *Human Reproduction* vol. 6 No. 9 1311–1326 (1991).

Anderson, T. et al., "Uterine Receptivity in the Primate" *Development of Preimplantation Embryos and Their Environment*, pp. 389–399 (1989).

Davies et al. J. Cell Biol., 109:1817–1826 (1989).

Pierschbacher et al. "Synthetic Peptide with Cell Attachment Activity of Fibronectin", *PNAS*, 80:1224–1227 (1983).

FIG. IA
FIG. IB
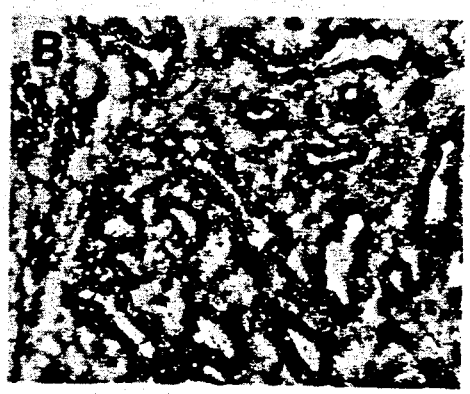
FIG. IC
FIG. ID
FIG. IE
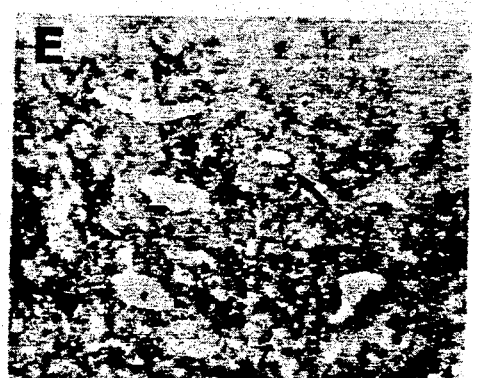
FIG. IF
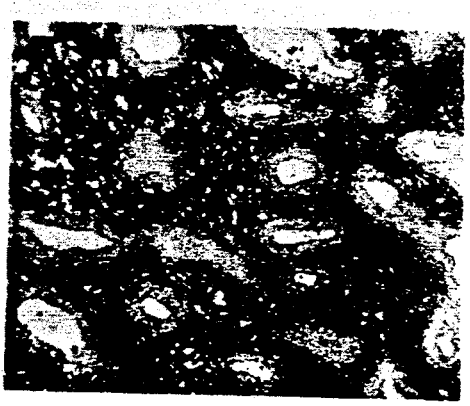

DETERMINATION OF ENDOMETRIAL RECEPTIVITY TOWARD EMBRYO IMPLANTATION

REFERENCE TO GOVERNMENT GRANTS

This work was supported in part by research grants from the Biomedical Research Support Grant Program, Division of Research Resources, the National Institutes of Health, grant number B.R.S.B. S07-RR-05415-29. The U.S. Government may have certain rights in this invention.

BACKGROUND OF THE INVENTION

Over the past decade, investigators have come to recognize the importance of the extracellular matrix (ECM) in directing the growth, differentiation and function of the overlying epithelium. Getzenberg et al., "The Tissue Matrix: Cell Dynamics and Hormone Action", *Endocrine Rev.*, 11:399–417 (1990). The interaction between cell and extracellular matrix (or substratum) is mediated by several classes of cell adhesion molecules, one of the most important being the integrins. Albelda et al., "Integrins and Other Cell Adhesion Molecules", *FESEB J.*, 4:2868–2880 (1990). Buck et al., "Integrin, a Transmembrane Glycoprotein Complex Mediating Cell-Substratum Adhesion", *J. Cell Sci. Suppl.*, 8:231–250 (1987). This diverse family of glycoprotein receptors is expressed on the cell membrane as heterodimeric $\alpha$ and $\beta$ subunits and is involved in both cell-cell and cell-substratum adhesion. Specific recognition and binding of extracellular matrix (ECM) components such as fibronectin (FN), laminin (LM) and collagen (Col) transmit information to the cytoskeletal structure, an interaction which may have major roles in promoting hormone responsiveness and genomic activation. Burridge et al., "Focal Adhesions: Transmembrane Junctions Between the Extracellular Matrix and the Cytoskeleton", *Ann. Rev. Cell. Biol.* 4: 487-525 (1988) and Getzenberg et al. supra.

Although extensive information exists about specific integrin proteins, for example, Hemler, M. E. "VLA Proteins in the Integrin Family: Structures, Functions and Their Role on Leukocytes", *Annu. Rev. Immunol:* 365–400 (1990), little is known concerning the distribution of these receptors in the female reproductive tract. In the uterus, the endometrium, composed of glandular epithelium and associated mesenchyme (stroma), maintains complex temporal and spatial functions in response to the cyclic hormonal milieu. The search for morphological or biochemical markers for uterine receptivity has been unsuccessful to date as reported by Rogers and Murphy, "Uterine Receptivity for Implantation: Human Studies", in *Blastocyst Implantation*, Yoshinaga, K. ed., Serono Symposia, pp. 231–238 (1989). Once such markers are identified, their role in endometrial phenomena including embryo implantation, fertility, contraception and endometrial maturation and receptivity can likely also be identified. Thus, as some integrins appear to meet the criteria for markers of receptivity there is a great need for methods of detecting integrin cell adhesion molecules in endometrium.

SUMMARY OF THE INVENTION

The present invention is directed to methods of detecting receptivity of endometrium to embryo implantation by detecting the B3 subunit of the $\alpha_v\beta_3$ integrin in endometrium with a monoclonal antibody.

Methods of diagnosing fertility and methods of monitoring endometrial maturation in a mammal are also provided by monitoring the appearance of the $\beta_3$ subunit of integrin in endometrium from a plurality of stages of the endometrial cycle. This is preferably done with a monoclonal antibody.

The present invention also provides methods of detecting the optimal window of embryo implantation in the endometrium by detecting the $\beta_3$ subunit of integrin in an endometrial sample, preferably with a monoclonal antibody.

Further aspects of the invention include methods of preventing embryo implantation by contacting the $\beta_3$ subunit of integrin in the endometrium with neutralizing Fab antibody fragments to $\beta_3$. Methods of in vitro fertilization are also embodiments of the invention. These comprise detecting the $\beta_3$ subunit of integrin in an endometrial sample, fertilizing an egg in vitro, and introducing the zygote into the uterus having endometrial tissue expressing the $\beta_3$ subunit.

Contraceptive and diagnostic kits are also contemplated hereby.

These and other aspects of the invention will become more apparent from the following detailed description when taken in conjunction with the following figures.

BRIEF DESCRIPTION OF THE DRAWINGS

FIG. 1A–1F depicts immunoperoxidase staining of normal endometrium. The photomicrographs depict the pattern of distribution for six different integrins that do not appear to change throughout the menstrual cycle. Dark areas represent positive staining, light areas represent absence of stain (absence of specific integrin subunit). Immunohistochemical staining of the collagen/laminin receptor subunits: $\alpha_2$(1A), $\alpha_3$(1B), $\alpha_6$(1C), and $\beta_4$(1D) shows prominent staining of epithelium (←) and microvessels (←) without significant stromal staining (*) for $\alpha_2$, $\alpha_3$, and $\beta_4$. Note basolateral staining $\alpha_6$ and basal staining for $\alpha_5$. Staining for fibronectin receptor subunits $\alpha_4$(E), $\alpha_5$(F) show predominant mesenchyme staining (*) with decreased epithelial staining (←). The immunoreactions (areas of dark staining) were developed by avidin-biotin- peroxidase complex using diaminobenzidine as a chromogen. For greater sensitivity, no counterstain was applied. Magnification: 125×.

FIG. 5A–6C depicts staining intensity of epithelial $\beta_3$ in 12 infertility patients with delayed endometrial maturation. Endometrium was collected from women undergoing evaluation for infertility. The biopsies were separated into two groups based on the correlation between histologic criteria and the menstrual cycle dating based on the time of ovulation and/or the subsequent menstrual period. Patients with endometrial biopsies 3 or more days "out of phase" (OOP group) were compared with 25 endometrial biopsies that were "in phase" (Normal) and shown in 3A. Sections were assigned a score of 0 (−; negative), 1 (±; weak), 2 (+; moderate) or 3 (++; strong), based on the intensity of epithelial $\beta_3$ staining. Examples of immunohistochemical staining of an "out of phase" biopsy (5B) and a normal "in phase" sample (5C) is included to contrast the epithelial $\beta_3$ staining in each group. Magnification: 400×.

FIG. 6A–6D exhibits immunoblot analysis of proliferative and secretory endometrium, stained for the $\beta_3$ subunit. (6A) Immunoblot of platelet extract (lane 1) compared with 2 samples from the early and mid proliferative phase (lanes 2,3) and from the luteal phase (lane 4 and 5; days 23 and 26, respectively) demonstrates a band at approximately 95 kD molecular weight, corresponding to $\beta_3$. Samples of endometrium were partially digested with collagenase and the glandular elements obtained (6B) using a modification of the methods of Satyaswaroop et al., "Isolation and Culture of Human Endometrial Glands", *J. Clin. Endocr. Metab.*, 48:639–641 (1979). The glands appear as hollow structures free from surrounding stroma. Immunofluorescence of samples from lanes 3 and 4 (6C and 6D, respectively) corresponds to the absence or presence of the 95 kD band in A. Magnification: 400×.

DESCRIPTION OF PREFERRED EMBODIMENTS

Figure 2A:
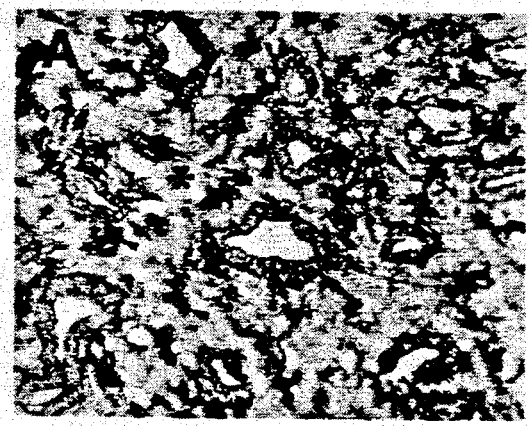
FIG. 2A–2C shows photomicrographs of the immunohistochemical staining for the integrin subunit $\alpha_1$ in proliferative vs. secretory endometrium. The staining in the glandular epithelium (←) was largely absent in the proliferative phase (2A), and pronounced in all sections after menstrual cycle day 14 (2B; day 20 endometrium). The microvasculature (←) staining was also pronounced, and did not change throughout the menstrual cycle. The staining noted in secretory endometrial glands was significantly higher than that of background (2C), Magnification: 125×.

The present invention is directed to methods of detecting receptivity of mammalian endometrium including obtaining a sample of endometrium, contacting the sample with a monoclonal antibody for the $\beta_3$ subunit of integrin and detecting the $\beta_3$ subunit.

For purposes of the present invention, the $\beta_3$ subunit may be $\beta_3$ alone or $\beta_3$ in combination with another integrin subunit, $\alpha_v$ for example.

As used herein integrin is defined as a diverse class of glycoprotein receptors expressed on the cell membrane. Integrins are cell adhesion molecules of the immunoglobulin superfamily. Integrins are composed of heterodimeric $\alpha$ and $\beta$ subunits and are involved in cell - cell and cell - extracellular matrix adhesion. The integrin family is a broadly distributed group of receptors composed of noncovalently associated $\alpha/\beta$ heterodimer pairs that mediate lekocyte - leukocyte and leukocyte endothelial cell adhesion, as well as cellular interactions with extracellular matrix components such as collagen, laminin, fibrinogen and fibronectin, and cell-cell interaction in organized tissues.

While integrins are found on virtually all cell types (the exception being red blood cells), expression of integrin subunits varies from cell type to cell type. In human uterine endometrium, as determined herein, glandular epithelial cells express primarily $\alpha_2$, $\alpha_3$ and $\alpha_6$ integrin subunits, which are collagen laminin receptors. Stromal cells express predominantly $\alpha_5$, fibronectin receptor. The presence of $\alpha_1$ on glandular epithelial cells is menstrual cycle specific, found only during the secretory phase. Expression of both subunits of the vitronectin receptor, $\alpha_v/\beta_3$, also undergoes menstrual cycle specific changes on endometrial epithelial cells. The expression of $\alpha_v$ increases throughout the menstrual cycle while the $\beta_3$ subunit appears abruptly on menstrual cycle day 20 on luminal and glandular epithelial cells.

The present invention is directed to endometrium of the uterus of a mammal. The uterine wall is largely smooth muscle or myometrium. The endometrium, a glandular layer of variable thickness extremely sensitive to the hormones estrogen/progesterone, lines the myometrium. The endometrium is composed of several functional layers. The layer nearest the myometrium is termed the basalis layer, and the layer closer to the surface known as the functionalis. This tissue is made of epithelial cells, stromal (or mesenchymal) cells and endometrial leukocytes. The epithelial cells are either glandular (forming glands beneath the surface of the endometrium) or luminal (lining the surface of the endometrium). These different types of epithelium serve different purposes and staining patterns for different marker proteins are not always the same between glandular and lminal. It is the luminal surface that would encounter the human embryo first and is thought to be involved in initial attachment. The endometrium of premenopausal girls and postmenopausal women is atrophic due to the lack of the hormones, estrogen and progesterone. In the reproductive-aged woman, the endometrium undergoes cyclic developmental changes based on the ovarian cycle of hormone release. The first day of menstruation is the first day of the cycle; menstruation is generally completed by day 5. The endometrial growth then resumes under the influence of estrogen and progresses through the day 14, proliferative phase, and on to about day 28. From day 14 to day 28 the endometrium also shows signs of increased gland growth and secretion, secretory phase, due largely to the influence of progesterone. During the follicular phase, while follicles are growing in the ovary, and estrogen is the dominant hormone, the endometrium grows thicker. With ovulation (typically day 14 of a 28 day cycle) the Women is exposed to estrogen plus progesterone. This is called the secretory or luteal phase, and is noted for a stereotypic series of histologic changes that proceeds as the cycle continues. These histologic changes are used by pathologists to date the endometrium, a process that remains controversial despite its use for the past 40 years. There have been no reliable immunohistochemicl markers reported that have proven utility in dating the endometrium.

Luteal phase dysfunction (LPD) is a term for developmental delay of the endometrium. It is a known cause of infertility, because of dyssynchrony between the fertilized egg and the endometrium. If an embryo is ready to attach but the endometrium is delayed, then pregnancy is not likely to occur. The causes for LPD include inadequate hormonal output by the ovary, and may implicate defective signalling from higher centers such as inadequate gonadotropic hormone output from the pituitary or hypothalamus. LPD is a known cause of infertility and spontaneous abortion and can be corrected with hormone augmentation.

Embryo implantation stages include: apposition—when the epithelial cells of the embryo attach to the outer (luminal) epithelial cells of the maternal endometrial surface; adhesion; and invasion of trophoblast into the underlying stroma where it established itself and begins to grow. Contact with maternal blood vessels is made to gain nutrients and oxygenated blood and to rid itself of waste products during the invasion stage. The stage of development that the embryo reaches at the time of implantation is the blastocyst stage, which occurs at the same time as hatching. There is evidence that hatching is required before implantation occurs, perhaps because the embryo must have its epithelial cells exposed (out of the zona pellucida shell) to interact with the maternal cell layers. As set forth herein, this interaction occurs via integrins.

For purposes of the current invention, mammals include, but are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

Monoclonal antibodies useful in the practice of the invention include any monoclonal antibodies having an affinity to or binding to the $\beta_3$ subunit of integrin. An example of such a monoclonal antibody is SSA6. Monoclonal antibody SSA6 may be produced as described by Bennett et al., *PNAS*, Vol. 80, 2417-2421 (1983).

Monoclonal antibodies which recognize $\beta_3$ combined with another integrin subunit may also be used. One such monoclonal antibody is 23C6, which may be prepared according to the method of Davies et al., *J. Cell Biol.*, Vol. 109, 1817-1826 (1989). Immunostaining with monoclonal antibodies such as 23C6 (specific to the intact $\alpha_v/\beta_3$ integrin, i.e. the vitronectin receptor) produces the identical pattern as SSA6 which only measures the $\beta_3$ subunit. This demonstrates that while $\alpha_v$ specific antibodies measure all the $\alpha_v$ containing integrins, antibodies which recognize the intact $\alpha_v/\beta_3$ integrin or the $\beta_3$ subunit can be used to study this integrin (the $\alpha_v/\beta_3$ "vitronectin receptor").

Other monoclonal antibodies can be used. The preparation of monoclonal antibodies is known to those in the art. Particularly, the method of Kohler and Milstein, *Nature*, 256: 495-497 (1975) may be used to produce monoclonal antibodies for use in the invention.

Methods of obtaining endometrial tissue samples for analysis, include any surgical and nonsurgical technique known in the art. Surgical methods include, but are not limited to biopsy, dilation and curettage. Nonsurgical methods include, but are not limited to, uterine washings and uterine brushings with immunocytochemical evaluation.

Methods of detecting $\beta_3$ in the endometrium include all methods of identifying glycoproteins known in the art. These methods include, but are not limited to, immunohistochemistry techniques such as immunoblotting or Western blotting, immunoperoxidase staining, fluorescein labeling, diaminobenzadine and biotinylation.

Generally, immunohistochemistry involves staining cryosectioned tissue samples. As used herein, endometrium samples may be cryosectioned to about 4-8$\mu$ thick. Endometrium is contacted with primary antibody, such as SSA6, followed by contact with secondary antibody, such as biotinylated goat anti-mouse antibody. Endometrium is then incubated in avidin-conjugated horseradish peroxidase macromolecular complex followed by chromagen incubation, such as diaminobenzadine. Fluorescein may then be added to observe integrin distribution.

Immunoblotting involves the analysis of protein, here integrin, on sodium dodecylsulfate-polyacrylamide gel electrophoresis SDS-PAGE. The gel is run under non-reducing conditions and the samples are transferred to a nitrocellulose membrane for example. The membrane is incubated in media containing primary antibody, such as SSA6. The filter is developed using a secondary antibody, such as alkaline phosphatase-conjugated goat anti-mouse antibody.

The methods of diagnosing infertility and for detecting the window for embryo implantation in the endometrium of a mammal are also within the scope of the invention. As provided herein, the $\beta_3$ subunit of integrin appears at day 20 of the menstrual cycle. It is also provided herein that $\alpha_v/\beta_3$ on endometrial epithelium binds fibronectin, vitronectin and osteopontin. These molecules may provide a bridge between the $\alpha_v/\beta_3$ integrin of the endometrium and the embryo. Further, patients with luteal phase dysfunction have delayed endometrial maturation, infertility and negative staining for $\beta_3$ on days 20 through 24. Thus, the optimal time for fertility may be determined by repetitively testing endometrial samples at a plurality of stages in the menstrual cycle. As such, screening for $\beta_3$ provides a method of diagnosing infertility and for detecting the window of embryo implantation in the endometrium. The window of implantation is that time when the endometrium of the uterus is available for embryo implantation. This window is preferably from day 19 to day 23, and more preferably day 20 of the human menstrual cycle, marked by the expression of $\alpha_v/\beta_3$ integrin.

Similar cycles are known for other mammals—it is within the ordinary skill in the art to adopt the foregoing methodology to such cycles.

The present invention is also directed to methods of in vitro fertilization. Once the $\beta_3$ subunit of integrin is detected in an animal selected for pregnancy, a fertilizable egg (or eggs) from the same or different animal could be replaced into the uterus to establish pregnancy. The egg and appropriate sperm are combined to produce a zygote in vitro. For purposes of the invention, in vitro fertilization may take place in a petri dish, in a test tube or the like. In addition, in vitro fertilization may also refer to independently adding eggs and sperm to the fallopian tubes such that the zygote is formed therein. In any event, the zygote is introduced to the uterus of the animal selected for pregnancy and monitored for implantation into the endometrium of the uterine wall.

Alternatively, the invention is directed to methods of preventing embryo implantation. Such may be carried out by contacting the endometrium with a neutralizing Fab fragment specific for $\beta_3$. For purposes of the present invention, Fab fragments from monoclonal antibodies which bind $\beta_3$ are within the scope of the invention. Fab fragments include, but are not limited to, Fab fragments from monoclonal antibodies SSA6 and 23C6. The Fab fragment may remain in vivo for a therapeutically effective time to prevent embryo implantation. The Fab fragment comprises the ligand binding portion of a monoclonal antibody for $\beta_3$, i.e. the binding site for $\beta_3$. A neutralized Fab fragment is used in place of a typical monoclonal antibody to reduce the possibility of an inflammatory reaction.

Contraception is a further embodiment of the invention. A contraceptive may include a therapeutically effective amount of neutralizing Fab fragment monoclonal antibodies specific for $\beta_3$ in a pharmaceutically acceptable carrier, preferably adapted for intrauterine application.

Compounds which specifically block binding of the embryo to this $\alpha_v/\beta_3$ receptor are also included within the scope of the present invention. Examples include peptides containing the amino acid sequence arginine - glycine - aspartic acid, RGD (Pierschbacher et al., "Synthetic Peptide with Cell Attachment Activity of Fibronectin", *PNAS*, Vol. 80, 1224–1227 (1983)) which is the active binding site for the vitronectin receptor. This sequence has been reported to block attachment of pregnancy derived cells (trophoblast) in vitro by researchers, Kao et al., "The Human Villous Cytotrophoblast: Interactions with Extracellular Matrix Proteins, Endocrine Function, and Cytoplasmic Differentiation in the Absence of Syncytium Formation", *Development*, Vol. 130, 693–702 (1988). Thus, a contraceptive containing the sequence RGD may be administered locally to prevent embryo implantation.

Pharmaceutically acceptable carriers include, and are not limited to, vaginal suppositories, intrauterine devices (IUD), gels such as slow release formulation, for example, depo forms of hormones—microcrystals injected and slowly released into the systemic circulation or delivered in silastic tubing. Contraceptive formulations would be administered in about 10 $\mu$g/ml.

Methods of monitoring endometrial maturation is also within the scope of the present invention. The endometrium may be monitored for embryo receptivity, embryo implantation, infertility, endometrial replenishment and ovulation.

Diagnostic kits are also within the scope of this invention. Such kits include monoclonal antibodies to rapidly detect $\beta_3$ in solution; an absorbant detection device which contains pre-absorbed antibody against $\beta_3$ and to which uterine washings can be applied; a developer to make $\beta_3$ visible when present.

The present invention is further described in the following examples. These examples are not to be construed as limiting the scope of the appended claims.

EXAMPLES

Human Sample

Endometrium was obtained from 35 reproductive age women at the time of hysterectomy. Tissue was obtained from the early proliferative (day 5) through late secretory phase (day 28) and all hysterectomies were performed for benign disease. Endometrial biopsies were performed on women as part of their evaluation for infertility. All patients were cycling normally and none had received hormones for at least 3 months prior to surgery. Dating of the endometrium was assessed according to the criteria of Noyes et al., "Dating the Endometrium", *Fertil. Steril.*, 1:3–8 (1950). Endometrial biopsies were evaluated in the context of timing of ovulation and/or the onset of the next menstrual period. Samples were judged as "out of phase" if histologic dating was delayed by 3 or more days relative to the predicted day of the menstrual cycle. Proliferative endometrium was categorized based on histology and on last menstrual period. Samples were transported on ice to the laboratory and were snap frozen on dry ice and stored at $-70°$ C.

Antibodies

Monoclonal antibodies (Mabs) PIH5, PIB5, PID6 specific to $\alpha_2$, $\alpha_3$, $\alpha_5$ subunits, respectively, were acquired from Drs. Elizabeth Wayner and William Carter. Mabs TS2/7 and B-5H10 directed against the $\alpha_1$ and $\alpha_4$ subunits, respectively were acquired from Dr. Martin Hemler. GoH3, a specific Mab directed against $\alpha_6$ was acquired from Dr. Arnoud Sonnenberg. Mab SSA6 specific to the $\beta_3$ subunit was acquired from Drs. Joel Bennett and James Hoxie. Mab LM142 against $\alpha_v$ was acquired from Dr. David Cheresh. The $\beta_4$ antibody was acquired from Dr. Steven Kennel. The 23C6 antibody which recognizes $\beta_3$ attached to $\alpha_v$ was obtained from Michael Horton.

Immunohistochemistry

Immunoperoxidase staining was performed on cryostat sections of endometrium samples from throughout the menstrual cycle. Serial cryosections 4–8$\mu$ thick were placed onto poly-L lysine coated slides, fixed in $-20°$ C. acetone for 10 minutes, and stained using Vectastain Elite ® ABC kits (Vector Laboratories, Burlingame, Calif.). Diaminobenzidine (DAB; Sigma Chemical Co., St. Louis, Miss.) was used as the chromagen. Primary antibody was placed on cryosections following blocking with 1% bovine serum albumin in PBS, and allowed to bind at room temperature for 1 hour. A phosphate buffered saline (PBS) pH 7.2 to 7.4 rinse was followed by secondary antibody consisting of biotinylated goat anti-mouse antibody for 30 minutes. Following a PBS rinse, the endogenous peroxidases were quenched with a 30 minute incubation with 0.3% $H_2O_2$ in absolute ethanol, followed by a 30 minute rehydration in PBS. Avidin:biotinylated horseradish peroxidase macromolecular complex (ABC) was then incubated on the sections for 30 minutes before adding diaminobenzadine for 3 minutes to complete the reaction. Some samples were treated with 1:200 dilution of fluorescein-labeled anti-mouse antibodies for 1 hr., for immunofluorescent microscopy. Samples were subsequently washed in PBS and mounted. The resulting staining was evaluated on a Nikon microscope at low (100x) and higher (400×) magnification with or without fluorescence. Staining was judged as absent (−), weak (±), moderate (+) or strong (++). Examples of each is presented in FIG. 3. Photomicrographs were made using Kodak T-MAX 100 ASA film.

Integrin Distribution in Normal Endothelium

The distribution of $\alpha_2$, $\alpha_3$, $\alpha_6$, and $\beta_4$ subunits of integrins which recognize primarily collagen (Col) and/or laminin (LM) is shown in FIG. 1 A-D. These subunits were present on glandular epithelium (←) throughout the menstrual cycle. Their distribution within the endometrium was typical of that seen for most epithelial tissues. The $\alpha_2$ and $\alpha_3$ subunits were distributed around the entire circumference of the cells, while the $\alpha_6$ and $\beta_4$ subunits appeared to be localized at the basolateral surface, adjacent to the basement membrane (BM) of the endometrial glands. The expression of these subunits by the mesenchyme (*) was less pronounced. While moderate staining was seen for $\alpha_6$ on stromal cells (FIG. 1 C) very little staining was noted for $\beta_4$. The expression of the $\alpha_4$ and $\alpha_5$ subunits of integrins known to bind fibronectin (Table 1) was quite restricted. The $\alpha_4$ subunit was undetectable above background staining (compare FIG. 1 E with FIG. 2C) in either epithelium or mesenchyme. The $\alpha_5$ subunit (FIG. 1F), representative of the classic fibronectin receptor was not seen on the epithelial components, but was strongly expressed in the mesenchyme which is rich in fibronectin.

TABLE 1
DISTRIBUTION OF ITEGRINS BY LIGAND SPECIFICITY

| | Ligands | |
|---|---|---|
| | Collagen/Laminin | Fibronectin/Vitronectin |
| Integrin Subunit | $\alpha_1/\beta_1$ | $\alpha_4/\beta_1$ |
| | $\alpha_2/\beta_1$ | $\alpha_5/\beta_1$ |
| | $\alpha_3/\beta_1$ | $\alpha_v/\beta_1$ |
| | $\alpha_6/\beta_1$ | $\alpha_v/\beta_3$ |
| | $\alpha_6/\beta_4$ | |

Figure 2B:
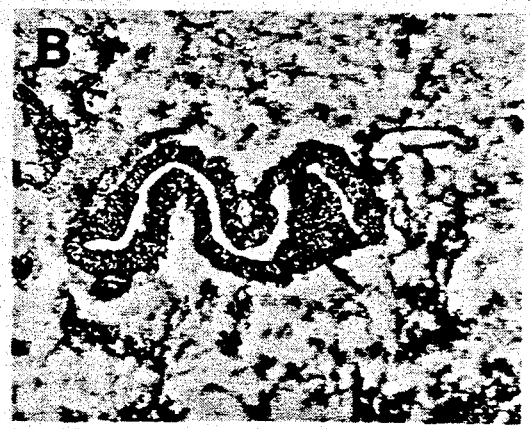
Figure 2C:
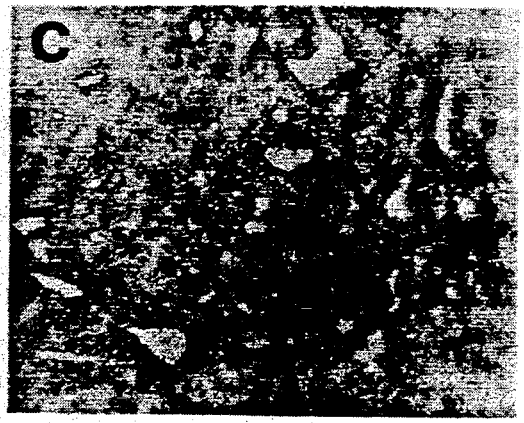
Figure 3B:
FIG. 3A–3D exhibits immunostaining of $\alpha_v$ and $\beta_3$ (the two pairing subunits of the vitronectin receptor integrin) in proliferative phase vs. secretory phase endometrium. The staining intensity of $\alpha_v$ in the proliferative phase (3A) was judged as "+" for the stromal cells (*) and "+" for glandular $\alpha_v$(←). Immunostaining for $\alpha_v$ in day 22 endometrium (3B) demonstrates a significant increase in glandular staining (example of "++" staining intensity). Likewise, the staining for $\beta_3$ was absent in proliferative epithelium (3C; ←) and was notably increased in this day 22 secretory endometrium (3D) Magnification: 125×.
Figure 3D:
Figure 3A:
Figure 3C:
Figure 4A:
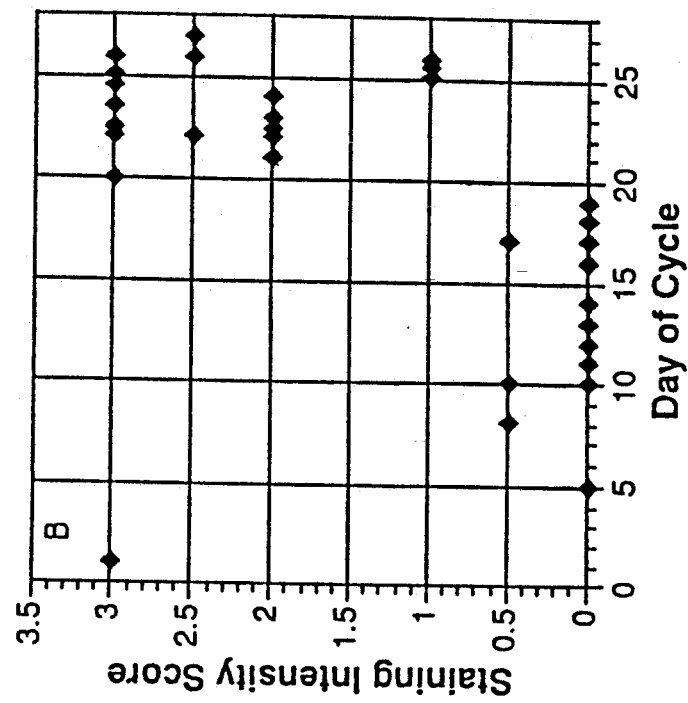
FIG. 4A–4B shows relative intensity of staining for the epithelial $\alpha_v$ and $\beta_3$ subunits in 35 endometrial samples throughout the menstrual cycle. The pattern of expression for $\alpha_v$ is shown in 4A, shows a gradual increase in staining throughout the menstrual cycle. In contrast, the pattern for $\beta_3$ in 4B, shows a more abrupt rise in this integrin subunit around day 20 of the menstrual cycle. Samples were staged according to the last menstrual cycle. Sections were assigned a score of 0 (−; negative), 1 (±; weak), 2 (+; moderate) or 3 (++; strong), by a blinded observer, and confirmed by a second observer.
Figure 4B:
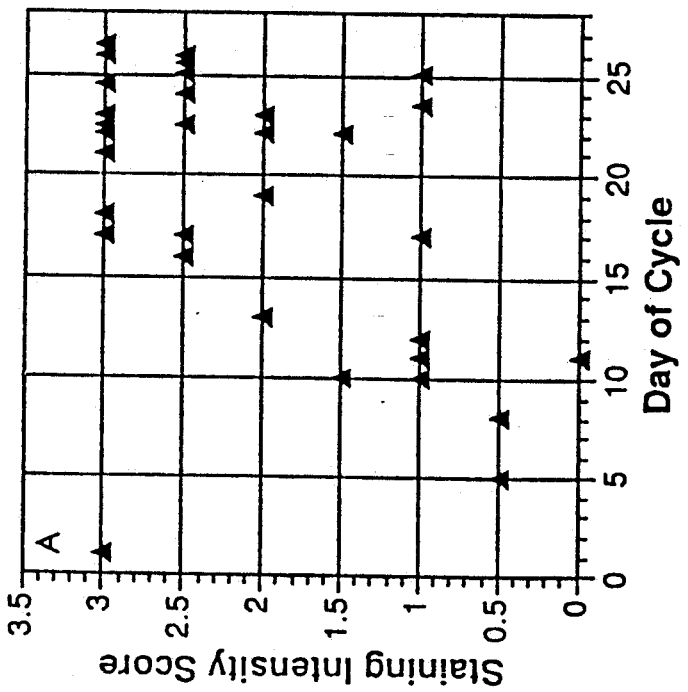

The intensity of immunostaining for three other subunits of integrins was found to change in a menstrual cycle-dependent manner. Immunostaining for $\alpha_1$ in the proliferative phase (FIG. 2A) was only slightly above background levels (FIG. 2C). The intensity of staining increased throughout the secretory phase (FIG. 2B). This intense circumferential staining was found on glandular and luminal epithelium on all samples from day 15 to 28. Likewise, $\alpha_v$ was weakly expressed on both the epithelium and mesenchyme in the proliferative phase (FIG. 3A) and staining increased gradually during the secretory phase to the level noted in FIG. 3B. During the proliferative phase $\beta_3$ staining was only present on the mesenchymal cells (FIG. 3C). Increased $\beta_3$ staining was apparent on the endometrial epithelium only after day 19 of the menstrual cycle (FIG. 3D) on the luminal as well as glandular epithelium, and was also present in a pericellular distribution. In contrast, the basalis layer did not significantly stain for either $\alpha_v$ or $\beta_3$. This changing pattern of epithelial $\alpha_v$ and $\beta_3$ throughout the cycle was studied in 35 endometrial samples and is depicted graphically in FIG. 4 A and B.

Collagen/laminin receptors (col/LM) characterized by $\alpha_2$, $\alpha_3$ and $\alpha_6$ were uniformly expressed throughout the menstrual cycle, see Table 2. The pericellular distribution of $\alpha_2$ and $\alpha_3$ subunits was distinctly different from that of $\alpha_6$ subunit. Characteristic of a laminin receptor, $\alpha_6$ was concentrated on the basolateral surface. The $\beta_4$ subunit which pairs with $\alpha_6$, was also found distributed on the basolateral surface of epithelial cells, and its distribution appeared even more restricted to the basal pole. The $\alpha_5/\beta_1$ integrin, a major fibronectin receptor, was also uniformly expressed throughout the menstrual cycle. Unlike the collagen and laminin receptors, the distribution of $\alpha_5/\beta_1$ was limited to the mesenchyme.

The temporal pattern of distribution of was varied. Immunostaining was first detected prior to the secretory phase with an increase in intensity throughout the cycle. One subunit known to pair with $\alpha_v$ is $\beta_3$. $\beta_3$ is not characteristically present on epithelial cells. The abrupt appearance of the subunit after day 19 suggests that expression of the vitronectin receptor is regulated in human endometrium. The increased epithelial $\alpha_v/\beta_3$ staining in normal cycles correlates to an implantation window within the secretory phase. While the physiologic basis for the implantation window has not been previously established, a proposed role of integrins in the initial interaction between maternal and embryonic cells indicates an endometrial period of receptivity.

TABLE 2
DISTRIBUTION OF INTEGRIN SUBUNITS IN NORMAL ENDOMETRIUM DURING THE MENSTRUAL CYCLE

Figure 5A:
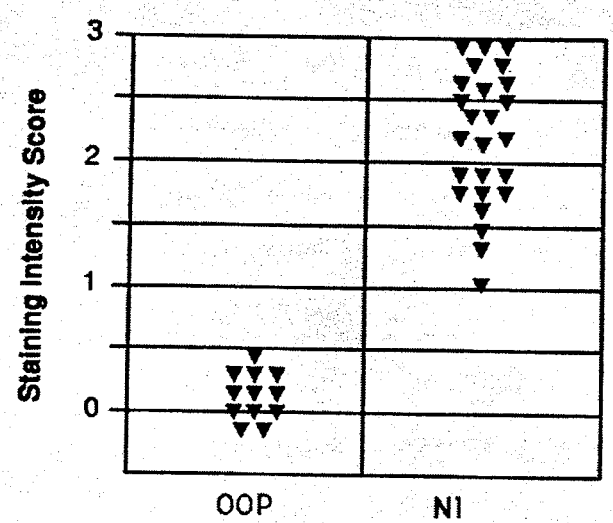
Figures 5B, 5C:
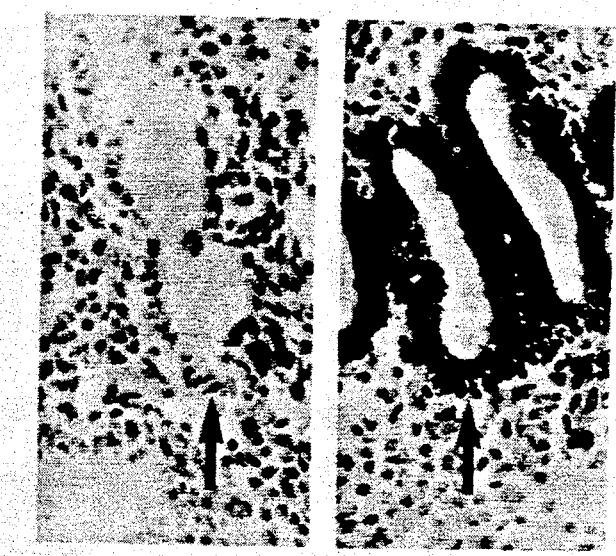

| | Col/LM | | | | | FN/VN | | | |
|---|---|---|---|---|---|---|---|---|---|
| Cell Type | $\alpha_1$ | $\alpha_2$ | $\alpha_3$ | $\alpha_6$ | $\beta_4$ | $\alpha_4$ | $\alpha_5$ | $\alpha_v$ | $\beta_3$ |
| Epithelial | | | | | | | | | |
| proliferative | o | . | . | .b | .b | o | o | o | o |
| early secretory | . | . | . | . | . | o | o | * | .o |
| late secretory | . | . | . | . | . | o | o | . | . |
| Stromal | o | o | o | . | o | o | . | . | |
| proliferative | | | | | | | | | |
| early secretory | o | o | o | * | o | o | * | . | . |
| late secretory | * | o | o | . | o | o | * | . | . | b = basolateral distribution of staining
. = + or ++ staining
* ± = staining
o = − staining Integrins in Discordant Endometrium The presence of the epithelial $\beta_3$ subunit appeared to be a consistent internal marker of luteal phase maturation, and the timing of $\beta_3$ expression correlated with the peri-implantation period or window of embryo implantation. To investigate whether this phenomenon would be useful in the clinical evaluation of endometrial biopsies, immunostaining was performed on luteal phase endometrial samples from cycles which showed evidence of maturational delay. Endometrial biopsies from 25 women who had concordance of menstrual and histologic dating ("Normal" group) were compared to 12 biopsies which were identified as $\geq 3$ days out of phase (OOP) based on either the time of ovulatory or the subsequent menses. Samples were immunostained for $\alpha_1$, $\alpha_v$ and $\beta_3$ subunits. All biopsies were performed on days 20 to 24 of the menstrual cycle. In all instances, immunostaining for these three antigens was present on endometrial epithelia from the normal group In biopsies which were delayed by 3 days or more, $\alpha_1$ and $\alpha_v$ staining was present, but epithelial $\beta_3$ staining was absent. The comparison of $\beta_3$ staining intensity in the two groups is shown in FIG. 5A. Accompanying photomicrographs of $\beta_3$ immunostaining from out of phase biopsies (OOP; B) and normal "in phase" biopsies (C) is included, which demonstrates the discrepancy seen in $\beta_3$ staining. In subsequent treatment cycles, 2 OOP patients underwent repeat biopsy during a normalized cycle at which time immunostaining for epithelial $\beta_3$ was present. This suggests that the lack of $\beta_3$ was not an intrinsic defect in the OOP group. Rather, the discordant biopsies which lacked $\beta_3$ had not yet established the mid-luteal phenotype of normal day 20 to 24 endometrium.

Cell Harvest and NP-40 Extraction

To further demonstrate that immunohistochemical staining accurately reflected changes in the expression of $\beta_3$ subunit on endometrial epithelium, immunoblots (Western blots) were performed on samples of enriched endometrial glandular elements from proliferative and secretory phase. Four samples of endometrium were obtained for the evaluation of the $\beta_3$ subunit in proliferative (n =2) and late secretory (n =2) endometrial epithelium. Each sample was placed in Dulbecco's modified Eagle's medium (DMEM; Sigma, St. Louis, Miss.), supplemented with 10% fetal bovine serum (Flow Laboratories, McLean, Va.) glucose (4500 mg/L), Hepes buffer (25 mM), L-glutamine (584 mg/L), and sodium bicarbonate (3.7 gms/L). Endometrium was minced in a plastic petri dish prior to incubation with 6 mg of collagenase (type 1A, 550 units/mg; Sigma, St Louis, Miss.) for 2 hours at 37° C. utilizing modifications of the procedures described by Satyaswaroop et al. in "Isolation and Culture of Human Endometrial Glands", *J. Clin. Endocr. Metab.*, 48:639–641 (1979). The resulting suspension was successively passed through a 250 µm sieve and a 38 µm sieve (Newark Wire Cloth Co, Newark N.J.). The course (250 µm) sieve removed undigested material, while the second retained the glandular elements and excluded the individual stromal and blood cells. After thorough rinsing, the glandular elements were obtained by backwashing with 10 to 20 ml of DMEM. The isolated glandular structures were then transferred to a 1.5 ml microfuge tube and centrifuged 3 times (82 × g) for 2 minutes with intermittent washes with PBS. Membrane extracts were prepared by adding small volumes 100-200 µl) of 10 mM Tris-acetate, pH 8.0, 0.5% NP-40, 0.5 mM $Ca^{2+}$ (TNC) with 2 mM PMSF (phenyl methyl-sulfonyl fluoride) to the final pellet, pipetted and incubated on ice for 15 minutes. The lysate was centrifuged for 5 minutes at 16,000 × g in a microcentrifuge. The resulting supernatant was called NP-40 extract and was frozen at −70° C. until use. A portion of the original, undigested tissue was cryosectioned for immunohistochemical localization of $\beta_3$.

Gel Electrophoresis and Immunoblots

The protein concentration of each NP-40 extract and an extract of platelets (positive control) was determined using technique described by Lowry et al., "Protein Measurement with Folin Phenol Reagent", *J. Biol. Chem.*, 193:265-271 (1951). Samples with equal amounts of protein were added to electrophoresis sample buffer (62.5 mM Tris base, 2% SDS, 10% glycerol, pH 6.8). Samples were analyzed by SDS-PAGE using 6% poyyacrylamide gels, using non-reducing conditions described by Laemmli, U. K., "Cleavage of Structural Proteins During Assembly of the Head of Bacteriophage T4", *Nature*, 227:680–685 (1970). The gel was transferred to nitrocellulose using a Biorad transfer apparatus (Biorad, Richmond, Calif.) and blocked with 4% BSA in PBS with 0.2% Na Azide for 1 hour. After addition of primary antibody (SSA6 supernatant) for 2 hours, the gels were developed using an alkaline phosphatase-conjugated secondary antibody (Promega Corp., Madison, Wis.) according to methods described by Albelda et al., "EndoCAM:A Novel Endothelial Cell-Cell Adhesion Molecule", *J. Cell Biol.*, 110:1227–1237 (1990).

Figure 6A:
Figure 6C:
Figure 6B:
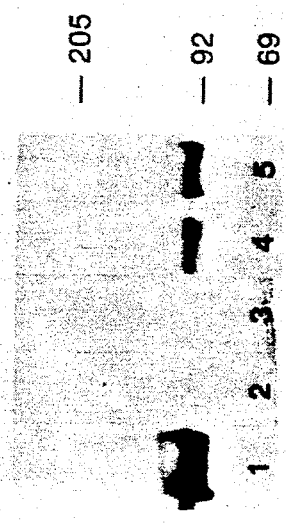
Figure 6D:

As shown in FIG. 6A, proliferative phase epithelial structures had little to no immunostaining at 95 kD (lanes 2 and 3), compared to the positive control (platelet extract; lane 1) or to samples from the secretory phase (lanes 4 and 5) which showed strong staining for $\beta_3$. The isolated endometrial glands appeared as tubular structures free of surrounding stroma (FIG. 6B). Immunofluorescent staining for $\beta_3$ from samples corresponding to lanes 3 and 4 (mid proliferative phase and day 23, respectively) are shown in FIG. 6C and D. Note the absence of glandular staining in the proliferative sample, while both glandular and luminal immunostaining is obvious from the secretory phase. These data confirm that the expression of epithelial $\beta_3$ in human endometrium is a cycle specific phenomenon.

Various modifications of th invention in addition to those shown and described herein will be apparent to those skilled in the art from the foregoing description. Such modifications are also intended to fall within the scope of the appended claims.

What is claimed:

1. A method for detecting receptivity of endometrium to embryo implantation comprising:
   a. obtaining a sample of said endometrium,
   b. contacting said sample with a monoclonal antibody specific for $\beta_3$ integrin,
   c. detecting the presence or absence of $\beta_3$ in said sample, and
   d. correlating the presence of $\beta_3$ with endometrial receptivity.

2. The method of claim 1 wherein said monoclonal antibody is SSA6.

3. The method of claim 1 wherein said $\beta_3$ is combined with another integrin subunit.

4. The method of claim 3 wherein said other integrin subunit is $a_v$.

5. The method of claim 4 wherein said monoclonal antibody is 23C6.

6. The method of claim 1 wherein said sample is a tissue section and said detecting step comprises immunohistochemically staining said sample with a labeled secondary antibody which binds the anti-$\beta_3$ antibody, wherein the presence of said label corresponds to the presence of $\beta_3$ integrin.

7. The method of claim 1 wherein said sample is a cell extract and said contacting said detecting steps comprise immunoblotting with said monoclonal antibody specific for $\beta_3$ integrin and labeled secondary antibody which binds the anti-$\beta_3$ integrin antibody, wherein the presence of said label corresponds to the presence of $\beta_3$ integrin.

8. The method of claim 1 wherein said endometrium is human.

9. A method for diagnosing infertility in a mammal comprising:
   a. obtaining a sample of endometrium from said mammal,
   b. contacting said sample with a monoclonal antibody specific for $\beta_3$ integrin,
   c. detecting the expression of $\beta_3$ in said sample,
   d. repeating steps a.-c. with samples of said endometrium at a plurality of stages of the menstrual cycle, and
   e. correlating the lack of $\beta_3$ expression with infertility.

10. The method of claim 9 wherein said monoclonal antibody is SSA6.

11. The method of claim 9 wherein said $\beta_3$ is combined with another integrin subunit.

12. The method of claim 11 wherein said other integrin subunit is $a_v$.

13. The method of claim 12 wherein said monoclonal antibody is 23C6.

14. The method of claim 9 wherein said mammal is human.

15. The method of claim 9 wherein said sample is a tissue section and said detecting step comprises immunohistochemically staining said sample with a labeled secondary antibody which binds the anti-$\beta_3$ antibody, wherein the presence of said label corresponds to the presence of $\beta_3$ integrin.

16. The method of claim 9 wherein said sample is a cell extract and said contacting and detecting steps comprise immunoblotting with said monoclonal antibody specific for $\beta_3$ integrin and labeled secondary antibody which binds the anti-$\beta_3$ integrin antibody, wherein the presence of said label corresponds to the presence of $\beta_3$ integrin.

17. The method of claim 9 wherein said stages of the menstrual cycle are selected from the group consisting of follicular phase and secretory phase.

18. A method of detecting the window of embryo implantation in endometrium comprising:
   a. obtaining a sample of endometrium,
   b. contacting said sample of endometrium with a monoclonal antibody specific for $\beta_3$ integrin,
   c. detecting the presence or absence of $\beta_3$ in said sample,
   d. repeating steps a.–c. with samples of endometrium at a plurality of stages of the menstrual cycle, and
   e. correlating the presence of $\beta_3$ with the window of embryo implantation.

19. The method of claim 18 wherein said monoclonal antibody is SSA6.

20. The method of claim 18 wherein said $\beta_3$ is combined with another integrin subunit.

21. The method of claim 20 wherein said other integrin subunit is $\alpha_v$.

22. The method of claim 21 wherein said monoclonal antibody is 23C6.

23. The method of claim 18 wherein said sample is a tissue section and said detecting step comprises immunohistochemically staining said sample with a labeled secondary antibody which binds the anti-$\beta_3$ antibody, wherein the presence of said label corresponds to the presence of $\beta_3$ integrin.

24. The method of claim 18 wherein said sample is a cell extract and said contacting and detecting steps comprise immunoblotting with said monoclonal antibody specific for $\beta_3$ integrin and labeled secondary antibody with binds the anti-$\beta_3$ integrin antibody, wherein the presence of said label corresponds to the presence of $\beta_3$ integrin.

25. A method of monitoring endometrial maturation in a mammal comprising:
   a. obtaining a sample of the endometrium,
   b. contacting said sample with a monoclonal antibody specific for $\beta_3$ integrin,
   c. detecting the appearance of $\beta_3$ in said sample,
   d. repeating steps a.–c. with samples of endometrium at a plurality of stages of the endometrial cycle, and
   e. correlating the appearance of $\beta_3$ integrin with endometrial maturation.

26. The method of claim 25 wherein said monoclonal antibody is SSA6.

27. The method of claim 25 wherein said $\beta_3$ is combined with another integrin subunit.

28. The method of claim 27 wherein said other integrin subunit is $\alpha_v$.

29. The method of claim 28 wherein said monoclonal antibody is 23C6.

30. The method of claim 25 wherein said sample is a tissue section and said detecting step comprises immunohistochemically staining said sample with a labeled secondary antibody which binds the anti-$\beta_3$ antibody, wherein the presence of said label corresponds to the presence of $\beta_3$ integrin.

31. The method of claim 25 wherein said sample is a cell extract and said contacting and detecting steps comprise immunoblotting with said monoclonal antibody specific for $\beta_3$ integrin and labeled secondary antibody which binds the anti-$\beta_3$ integrin antibody, wherein the presence of said label corresponds to the presence of $\beta_3$ integrin.

32. The method of claim 25 wherein said stages of the endometrial cycle are selected from the group consisting of follicular phase and secretory phase.

* * * * *

UNITED STATES PATENT AND TRADEMARK OFFICE
CERTIFICATE OF CORRECTION

PATENT NO. : 5,279,941
DATED : January 18, 1994
INVENTOR(S) : Bruce Lessey

It is certified that error appears in the above-indentified patent and that said Letters Patent is hereby corrected as shown below:

Column 2, line 1, delete "$\alpha_v\beta_3$" and replace with --$\alpha_v/\beta_3$--
Column 2, line 41, delete "$\alpha_5$" and replace with --$\beta_4$--
Column 2, line 64, delete "+" and replace with --$\pm$--
Column 4, line 63, "delete "immunohistochemicl" and
    replace with --immunohistochemical--
Column 9, line 65, after "distribution of" insert --$\overline{\alpha_v}$--
Column 10, line 2, after "the" insert --$\beta_3$--
Column 10, line 42, delete "$\geq$" and replace with -->--
Column 10, line 48, after "group" insert --.--

Signed and Sealed this

Eleventh Day of July, 1995

Attest:

BRUCE LEHMAN

Attesting Officer    Commissioner of Patents and Trademarks